Figure 1:
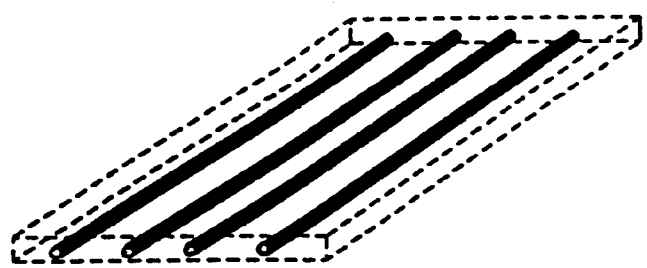

United States Patent
Bodenschatz et al.

[11] Patent Number: 6,074,965
[45] Date of Patent: *Jun. 13, 2000

[54] SUPPORT MATERIAL FOR MEDICAL PURPOSES

[75] Inventors: Stefan Bodenschatz; Peter Himmelsbach, both of Buxtehude, Germany

[73] Assignee: Beiersdorf AG, Hamburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/699,273

[22] Filed: Aug. 19, 1996

[30] Foreign Application Priority Data

Aug. 25, 1995 [DE] Germany .......................... 195 31 291

[51] Int. Cl.[7] ....................................... A61L 15/07
[52] U.S. Cl. ................. 442/269; 442/305; 442/269; 428/317.9; 428/295.4; 428/297.4; 428/297.1; 428/902; 602/41; 602/44; 602/45; 602/46; 602/76; 602/77

[58] Field of Search .................... 428/902, 304.4, 428/295.4, 297.4, 297.1, 317.9; 442/269, 304, 305, 370; 604/304; 602/41, 44, 45, 46, 76–77

[56] References Cited

U.S. PATENT DOCUMENTS 4,668,563  5/1987  Buese et al. ............................ 428/902

*Primary Examiner*—Elizabeth M. Cole
*Attorney, Agent, or Firm*—Norris, McLaughlin & Marcus, P.A.

[57] ABSTRACT

Support material for medical purposes, which is characterized in that an addition of high-strength fibers or threads on an organic or inorganic base with a maximum tensile strength over 60 cN/tex gives the support material a maximum tensile strength of over 2 N/cm and the support material has mainly a maximum tensile strength of under 400%.

15 Claims, 1 Drawing Sheet

SUPPORT MATERIAL FOR MEDICAL PURPOSES

The invention relates to a support material for medical purposes, chiefly bandages, adhesive strips, plasters or dressings.

Numerous materials based on films, fabrics, knit goods, fleeces, gels or foams are known and used in practice as support materials for these purposes. The materials, which often are also coated with a self-adhesive composition, must be compatible with the skin, permeable to air and water vapor as a rule, as well as pliable and able to conform to shapes. Due to these requirements a very thin or soft support is often preferred. For handling and in use, however, the support materials must also have sufficient strength and in some cases a limited stretchability.

Thin supports, especially those made of batting regarding strength and elongation at breakage, even though the support in itself does not.

This object is achieved by adding to the support materials high-strength fibers or threads with a maximum tensile strength of 60 cN/tex, which give the material a maximum tensile strength of at least 2N/cm. The maximum elongation (elongation at breakage) of the supports according to the invention is then preferably less than 400%.

Thus, support materials whose use has formerly been impossible for lack of strength and/or excessive elongation become usable for medical purposes.

The known supports made of fabric, knit goods, films, batting, foam, gels or products made therefrom by lamination can be used as support materials, if they otherwise satisfy the requirements of medical use.

The high-strength fibers or threads can consist of organic and inorganic materials, for example, and preferably, glass, carbon or also special polyamides.

The threads can be used in the form of monofilaments, multiple filaments or spun fiber yarn, and the fibers for example in an oriented form. They should be bonded to the support material. This can be accomplished by the direct incorporation of the fibers or threads into the supports, such as by weaving them in in the case of wovens, knitting them in in the case of knits, embedding or incorporating them in the process of manufacture of films, gels or foams and batting.

The fibers or threads, however, can be post-bonded to the support, for example by lamination with an appropriate bonding layer. Embedment into the adhesive coating, for example, is also a possibility.

The number of the laminated or embedded threads or fibers depends primarily on the intended application and the desired maximum tensile strength as well as the maximum stretch of the support material, its particular nature, and the strength of the fibers and threads themselves, and therefore it may vary within relatively wide limits. They are preferably incorporated in accordance with the direction in which the support material is stressed, i.e., lengthwise. They can also, if it is better for the purpose, run only in the transverse or oblique direction or, for example, they can run in curves, spirals or in zig-zag or random orientation. And it may be desirable and it is possible for the support material to be able to be manually ripped perpendicularly to the orientation of the reinforcement and/or in the direction of the orientation.

As support material for a functional tape bandage, for example, a flexible support material woven from cotton can be used, to which carbon or glass threads are added according to the invention. Thus every second to tenth warp thread can consist of the high-strength material. With this design the support remains pliable and supple. At the same time it has a high strength and its stretch in the direction of stress is decidedly reduced. Due to the brittleness of the high-strength threads the fabric can still be ripped by hand.

A support of this sort appropriate for tapes has, for example, a maximum tensile strength of at least 60 N/cm, preferably 80 to 100 N/cm, and a maximum tensile elongation of less than 25%, preferably 5 to 10%, with a weight of less than 140 $g/m^2$, preferably less than 100 $g/m^2$.

In another possible embodiment, the woven fabric consists of 100% high-strength materials in the warp, and results in tape supports with an especially high tensile strength and low stretch.

By embedding or laminating the high-strength fibers or threads with batting or films, support materials can be produced which are also suitable for use as tapes. In the case of ready-made tape bandages the reinforcing threads or fibers are preferably arranged equally corresponding to the direction of stress in the applied state. Since these bandages are already cut or stamped to size, they do not need to be tearable.

Although in the case of tape bandages the material cannot be too thin if it is to satisfy the stringent requirements, if the tapes are to be used as roll plasters and first-aid bandages with absorbent pads for wounds, much lighter materials can be used, especially those based on non woven fabric or film which are made sufficiently stable by the addition of the high-strength threads or fibers.

A support suitable as material for casting plasters is, for example, one on the basis of woven acetate which by the addition is given a maximum tensile strength of more than 40 N/cm, preferably 60 to 80 N/cm, and a maximum stretch of less than 80%, preferably 20 to 30%, with a specific weight of no more than 90 $g/m^2$, preferably 70 to 50 $g/m^2$.

By laminating, incorporating or embedding high-strength fibers or threads into batting or films, supports of low specific weight under 70 $g/m^2$, preferably under 40 $g/m^2$, can be prepared with sufficient strength (maximum tensile strength at least 2 N/cm at a maximum elongation of under 400%) for first-aid bandages.

The use of high-strength reinforcing threads or fibers is appropriate especially for applications in which a thin, flexible, inexpensive support for medical purposes is desired which will have sufficient strength and low stretch.

Depending on the application, the reinforced support materials are coated if desired with one of the known skin-compatible adhesive compositions based on rubber or synthetic polymers, and also in some cases they are provided with an absorbent pad and packaged in the usual manner.

The invention is further described in connection with the accompanying drawing wherein FIGS. 1 to 4 show different reinforcing patterns.

Referring to the drawing more specifically, in each of the FIGS. 1 to 4 a base material is shown in dotted lines.

Figure 2:
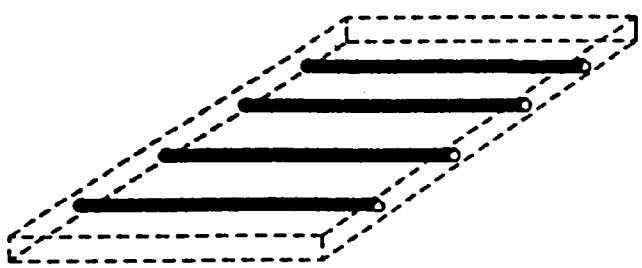
Figure 3:
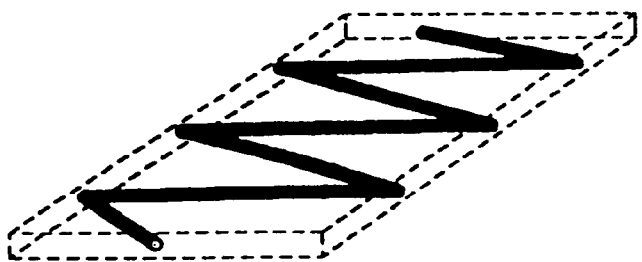
Figure 4:
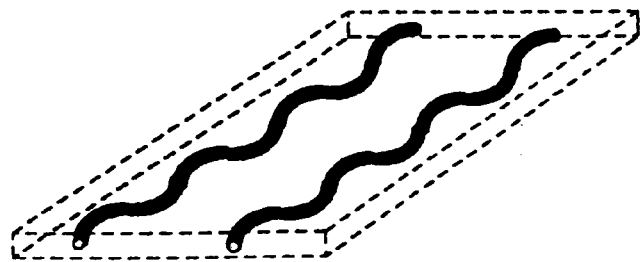

The heavy lines indicate the reinforcing threads, in FIG. 1 linear lengthwise, in FIG. 2 linear transverse, in FIG. 3 in zig zag form progressing lengthwise and in FIG. 4 sinuous progressing lengthwise.

It will be understood that the specification and examples are illustrative but not limitative of the present invention and that other embodiments within the spirit and scope of the invention will suggest themselves to those skilled in the art.

We claim:

1. Pliable support material for medical purposes comprising an organic base of batting, woven material, film, foam, gel or knit goods, and having, in addition to said base, high-strength fibers and/or threads with a tensile strength of more than 60 cN/tex added thereto, said support material having a tensile strength of over 2 N/cm and a tensile elongation under 25%, said support material remaining pliable throughout its use for said medical purposes.

2. Pliable support material for medical purposes according to claim 1, wherein the support material is strenghtened with a thread or a plurality of threads of monofilament, multifilament or spun fiber yarn.

3. Pliable support material for medical purposes according to claim 1, characterized in that the support material is strengthened with oriented fibers.

4. Pliable support material for medical purposes according to claim 1, characterized in that the fibers or threads consist of glass, carbon or polymides.

5. Pliable support material for medical purposes according to claim 1, characterized in that the support material is laminated with the threads and/or fibers.

6. Pliable support material for medical purposes according to claim 1, characterized in that the threads and/or fibers are incorporated into the support material.

7. Pliable support material for medical purposes according to claim 1, characterized in that the threads and/or fibers are embedded into the support material.

8. Support material for medical purposes according to claim 1, wherein the support material can be torn by hand perpendicularly to and/or not perpendicularly to the threads and/or fibers.

9. Pliable support material for medical purposes according to claim 1, wherein, when said support material is stressed in use, said stress is in a direction and the threads and/or fibers are aligned in the direction of stress on the support material.

10. Pliable support material for medical purposes according to claim 1, wherein said support material is used for tape bandages.

11. Pliable support material for medical purposes according to claim 1, wherein said support material is used for roll plasters.

12. Pliable support material for medical purposes according to claim 1, wherein said support material is used for first-aid bandages.

13. Pliable support material for medical purposes according to claim 1, wherein the tensile strength is over 40 N/cm.

14. Pliable support material for medical purposes according to claim 1, wherein the tensile elongation is at a specific weight of under 140 g/m$^2$.

15. Pliable support material for medical purposes comprising an organic or inorganic base of batting, woven material, foam or knit goods having, in addition to said base, high-strength fibers and/or threads with a tensile strength of more than 60 cN/tex added thereto, said support material having a tensile strength of over 2 N/cm and a tensile elongation under 25% at a specific weight of under 140 g/m$^2$.

* * * * *